United States Patent [19]

Kurjan et al.

[11] Patent Number: 5,763,267

[45] Date of Patent: Jun. 9, 1998

[54] APPARATUS FOR THE LARGE SCALE GROWTH AND PACKAGING OF CELL SUSPENSIONS AND THREE-DIMENSIONAL TISSUE CULTURES

[75] Inventors: Christine Kurjan, Palo Alto; Mark A. Applegate, San Diego; James H. Flatt, Del Mar; Dawn Orton Applegate, San Diego; Nicole Bloom, San Francisco; Mark Baumgartner, San Diego, all of Calif.

[73] Assignee: Advanced Tissue Sciences, La Jolla, Calif.

[21] Appl. No.: 632,972

[22] Filed: Apr. 16, 1996

[51] Int. Cl.[6] .................... C12M 1/32; C12M 1/22; C12C 1/00

[52] U.S. Cl. .................... 435/293.1; 435/297.2; 435/304.2; 435/399

[58] Field of Search .................... 210/456, 321.86, 210/321.75; 435/293.1, 297.2, 304.1, 304.2, 240.2, 325, 399

[56] References Cited

U.S. PATENT DOCUMENTS

| | | | |
|---|---|---|---|
| 3,734,851 | 5/1973 | Matsumura | 210/22 |
| 4,417,861 | 11/1983 | Tolbert | 417/315 |
| 4,639,422 | 1/1987 | Geimer et al. | 435/286 |
| 4,988,623 | 1/1991 | Schwarz et al. | 435/286 |
| 5,026,650 | 6/1991 | Schwarz et al. | 435/286 |
| 5,043,260 | 8/1991 | Jauregul | 435/1 |
| 5,081,035 | 1/1992 | Halberstadt et al. | 435/284 |
| 5,153,131 | 10/1992 | Wolf et al. | 435/240.24 |
| 5,153,132 | 10/1992 | Goodwin et al. | 435/240.24 |
| 5,153,133 | 10/1992 | Schwarz et al. | 435/240.24 |
| 5,155,034 | 10/1992 | Wolf et al. | 435/240.24 |
| 5,155,035 | 10/1992 | Schwarz et al. | 435/240.24 |
| 5,230,693 | 7/1993 | Williams et al. | 600/36 |
| 5,266,480 | 11/1993 | Naughton et al. | 435/240.243 |
| 5,308,764 | 5/1994 | Goodwin et al. | 435/240.24 |
| 5,416,022 | 5/1995 | Amiot | 435/284 |

FOREIGN PATENT DOCUMENTS

| | | | |
|---|---|---|---|
| WO 90/13639 | 11/1990 | WIPO | C12N 5/00 |
| WO 92/11355 | 7/1992 | WIPO | C12N 5/02 |
| WO 93/01843 | 2/1993 | WIPO | A61L 33/00 |
| WO 93/12805 | 7/1993 | WIPO | A61K 37/00 |
| WO 93/18132 | 10/1993 | WIPO | C12M 3/00 |
| WO 94/25584 | 11/1994 | WIPO | C12N 11/08 |

OTHER PUBLICATIONS

Atkinson et al.; *Biochemical Engineering and Biotechnology Handbook;* pp. 476–487 (1991).

Halberstadt et al., "The In Vitro Growth of a Three–Dimensional Human Dermal Replacement Using a Single–Pass Perfusion System," *Biotechnology and Bioengineering* 43:740–746 (1994).

*Primary Examiner*—Lynette F. Smith
*Assistant Examiner*—Brett Nelson

[57] ABSTRACT

An apparatus for the large scale culturing and packaging of cell suspensions, three dimensional tissue, and other biological systems is disclosed. The apparatus includes a plurality of flexible or semi-flexible treatment chambers comprising one or more individual culture pockets, a plurality of rigid spacers, an inlet fluid manifold, an outlet fluid manifold, a fluid reservoir, and a means for transporting fluid within the system. During treatment, liquid media is transported from the fluid reservoir to the inlet manifold, which will in turn evenly distribute the media to each of the connected treatment chambers and internal culture pockets. An outlet fluid manifold is also provided to ensure that each treatment chamber is evenly filled and to ensure that any air bubbles formed during treatment are removed from the treatment chambers. The treatment chambers are flexible or semi-flexible so as to provide for easy end-user handling during rinsing and application of the cultured transplants. Due to the flexibility of the treatment chambers, rigid spacers are also provided which ensure even fluid distribution within the chambers during treatment.

24 Claims, 17 Drawing Sheets

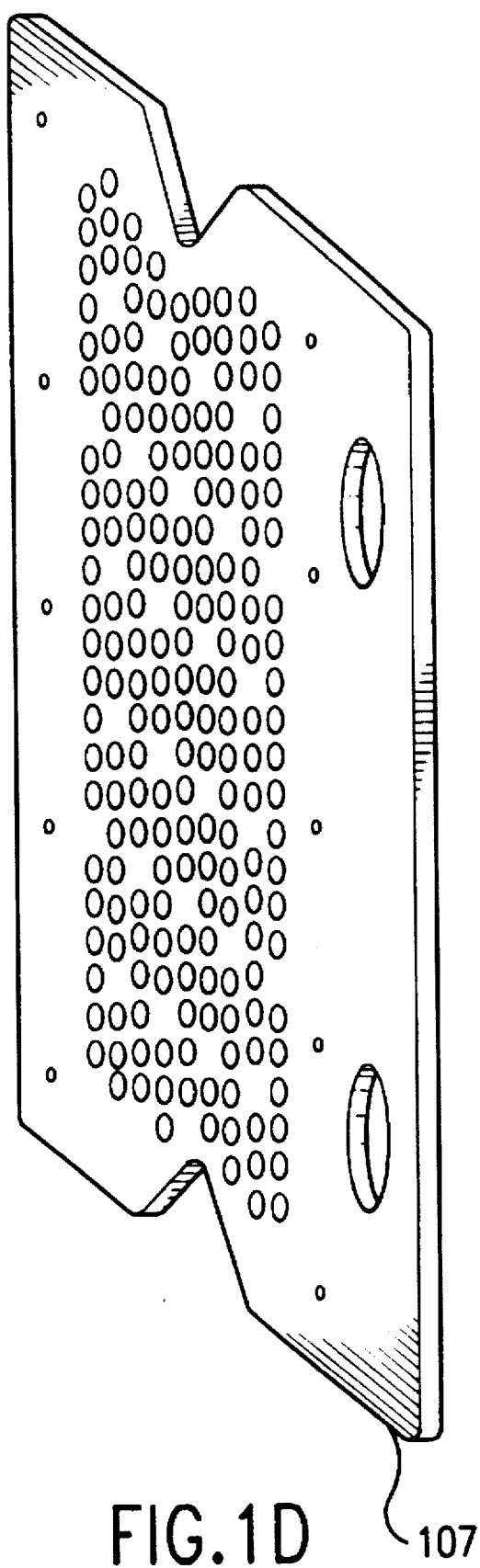
FIG.1D ⌐107

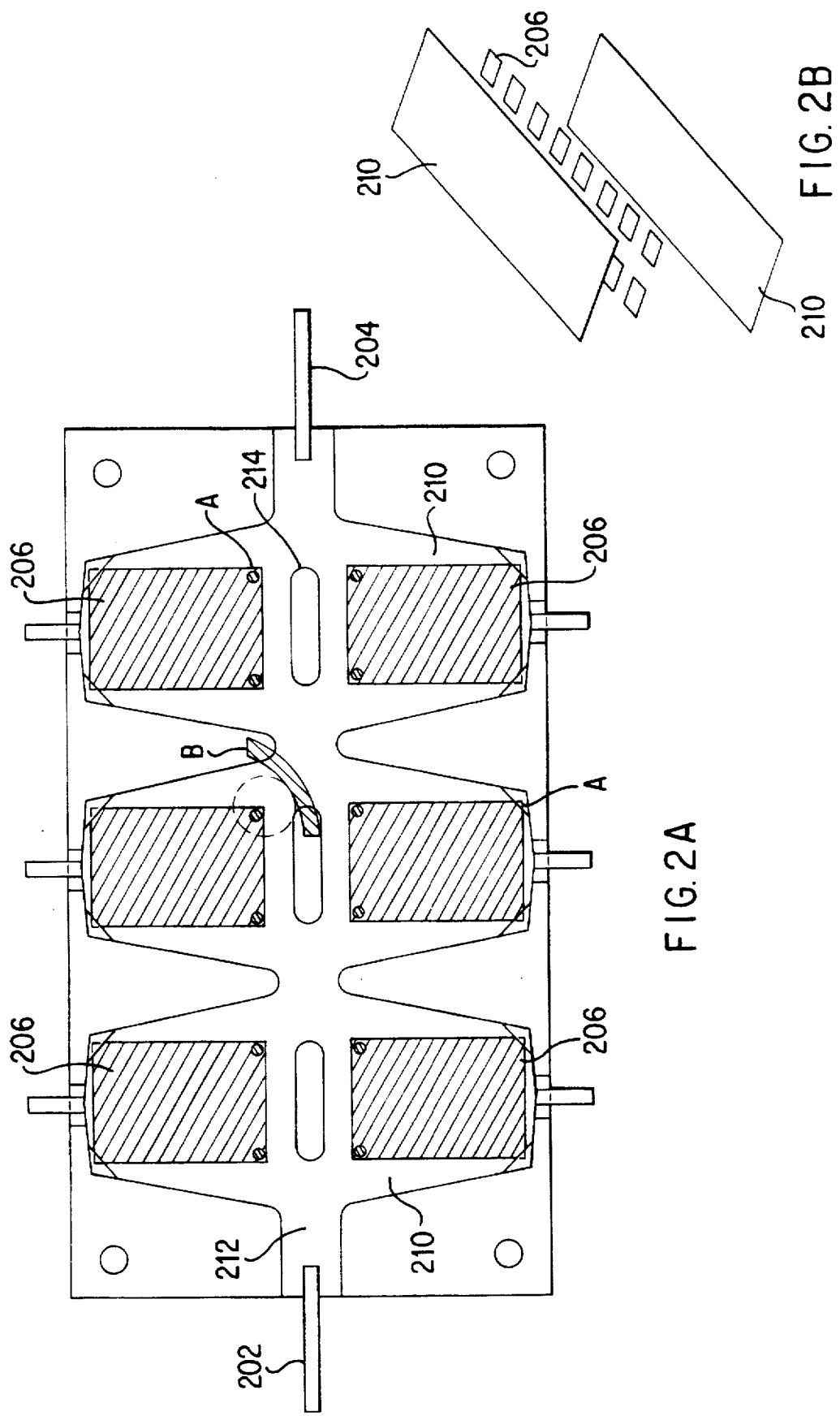

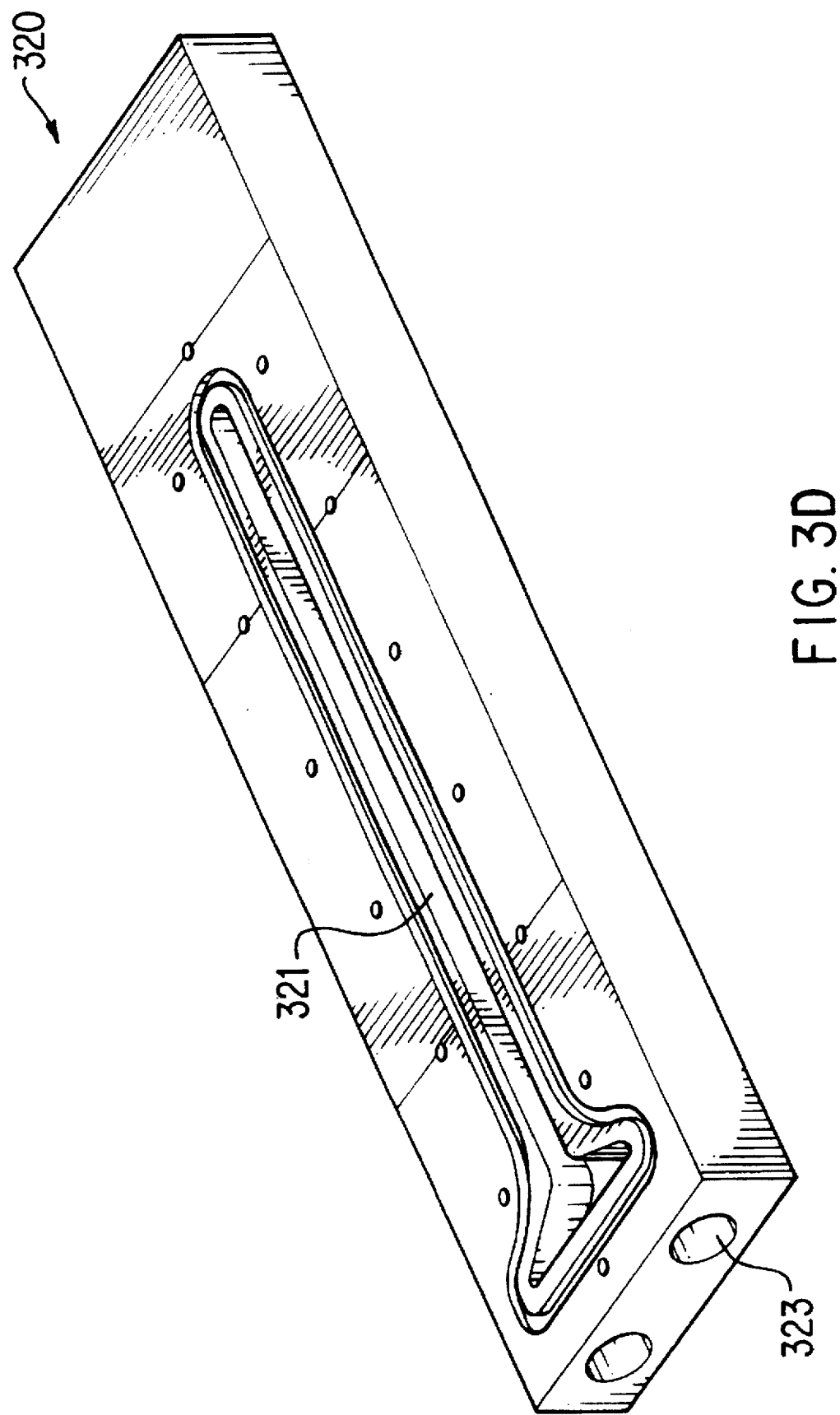

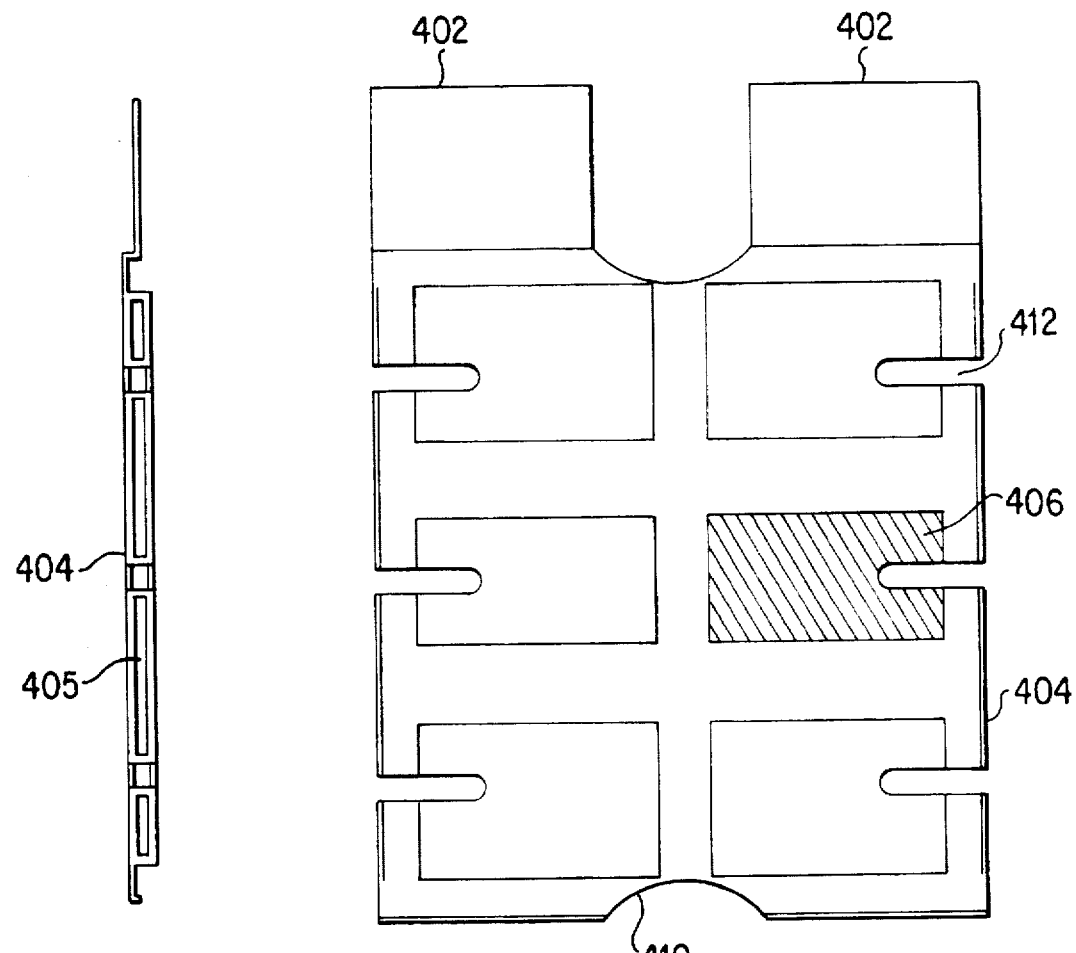
FIG. 4C
FIG. 4B
FIG. 4D

APPARATUS FOR THE LARGE SCALE GROWTH AND PACKAGING OF CELL SUSPENSIONS AND THREE-DIMENSIONAL TISSUE CULTURES

BACKGROUND OF THE INVENTION

1. Technical Field

The present invention relates to an apparatus for the growth and packaging of cell suspensions and three-dimensional tissue cultures. Specifically, the present invention relates to a system for the large-scale culturing and packaging of cell suspensions for cell-based and gene-based therapies, as well as for the culturing and packaging of human-engineered tissue constructs for a variety of transplant applications.

2. Discussion of the Related Art

The seeding and culturing of tissue for use in replacement therapy is known in the art. For example, U.S. Pat. No. 5,266,480 to Naughton et al. discloses the establishment of a three dimensional matrix, seeding of the matrix with desired cells, and maintenance of the culture to provide a variety of three-dimensional tissues suitable for use in different applications. Three-dimensional tissue has a number of uses, including use of the tissue for treatment of burn victims and for treatment of skin ulcers often associated with diabetes.

Culturing of human or animal cell suspensions for cell-based and gene-based therapies is also known in the art. For example, in an article entitled "Effect of Autolymphocyte Therapy on Survival and Quality of Life in Patients With Metastatic Renal-Cell Carcinoma," *The Lancet*, Vol. 335, No. 8696, pp. 994–98 (Apr. 28, 1990), a method is disclosed in which suspended lymphocytes are cultured in medium containing supernatant from a culture of mononuclear cells treated with mitogenic agents, grown for several days, and gamma-irradiated immediately prior to infusion in patients. Cell-based and gene-based therapies have a number of uses, including use of the cells for treatment of metastatic kidney cancer and for treatment of renal cell cancer.

Conventional means of tissue and cell culture have been limited by the need for human supervision and control of the media which feeds nutrients to the tissue and cells over the time needed for the growth of the same, which limits the amount of cells and tissue that can be cultured at a single time. For example, in an article entitled "The In Vitro Growth of a Three-Dimensional Human Dermal Replacement Using a Single-Pass Perfusion System" 43 Biotechnology and Bioengineering 740–746 (April 1994), a closed, single pass perfusion system is disclosed in which growth medium is passed through a parallel configuration of Teflon™ bag bioreactors. Each bag bioreactor contains a biodegradable mesh on a Teflon™ frame, onto which tissue is grown. The related art system described provides for 16 bag bioreactors, which must be carefully handled to avoid damaging the tissue as it grows.

SUMMARY OF THE INVENTION

It is therefore an object of the present invention to provide a system which allows for the large-scale culturing and packaging of cell suspensions and three-dimensional tissue in a convenient form which enables aseptic large-scale culturing, individual packaging, freezing, storing, shipping, and use.

It is a further object of the invention to provide a closed aseptic environment from culture initiation to end use.

It is yet a further object of the invention to provide a consistent culturing environment for the uniform culture of both cell suspensions and tissue.

In accordance with the present invention, there is provided an apparatus for the large scale culturing and packaging of cell suspensions and three dimensional tissues. The apparatus according to the invention includes a plurality of flexible treatment chambers, a plurality of rigid spacers, an inlet fluid manifold, an outlet fluid manifold, a fluid reservoir, and a means for transporting fluid from the reservoir to the treatment chambers. During treatment, liquid media is transported from the fluid reservoir to the inlet manifold, which will in turn evenly distribute the media to each of the connected treatment chambers. An outlet fluid manifold is also provided to ensure that each treatment chamber is evenly filled and to ensure that any air bubbles formed during media transport are removed from the treatment chambers.

The treatment chambers are advantageously flexible so as to provide for gas permeability, and thus, large scale culturing through the use of minimal mechanical components. Treatment chamber flexibility is additionally advantageous in that it allows for easy end-user handling during rinsing and application of the cultured transplants. Due to the flexibility of the treatment chambers, rigid spacers are also provided which ensure even fluid distribution within the chambers during treatment.

In this manner, the invention advantageously utilizes a compact and mechanically non-complex apparatus to maintain an aseptic and uniform environment for the large-scale culturing and individual packaging of cell suspensions, three dimensional tissues, and other biological systems.

BRIEF DESCRIPTION OF THE DRAWINGS

These and other features, aspects, and advantages of the present invention will become more readily apparent from the following detailed description, which should be read in conjunction with the accompanying drawings in which:

FIGS. 1A–1D illustrate a first exemplary embodiment of a system for the large scale culturing and packaging of cell suspensions and three dimensional tissues, wherein FIGS. 1A and 1B are perspective views of the system, FIG. 1C is a perspective view of the system with one end plate removed, and FIG. 1D is an alternative embodiment of a single rigid spacer;

FIGS. 2A–2B illustrate a first embodiment of a treatment chamber, wherein FIG. 2A is a top plan view of the treatment chamber, and FIG. 2B is a perspective view of the components of the treatment chamber prior to manufacture of the chamber;

FIGS. 3A–3D illustrate an alternative exemplary embodiment of a system for the large scale culturing and packaging of cell suspensions and three dimensional tissues, wherein FIG. 3A is perspective view of the system including rigid spacers, FIG. 3B is a perspective view of the system without rigid spacers, FIG. 3C is a perspective view of an inlet fluid manifold, and FIG. 3D is a perspective view of a fluid inlet piece of the inlet fluid manifold;

FIGS. 4A–4D illustrate a rigid spacer for use in a culturing system, wherein FIG. 4A is a perspective view of the rigid spacer, FIG. 4B is a top plan view of the rigid spacer, FIG. 4C is a side view of the rigid spacer, and FIG. 4D is an end view of the rigid spacer;

FIGS. 5A–5J illustrate yet another alternative embodiment of a system for the large scale culturing and packaging of cell suspensions and three dimensional tissues, wherein FIG. 5A is perspective view of the system, FIG. 5B is a perspective view of the system with the outlet manifold removed, FIG. 5C is a perspective view of a bottom portion of an inlet fluid manifold, FIG. 5D is a top plan view of a center portion of an inlet fluid manifold, FIG. 5E is top plan view of a lock plate for a manifold, FIG. 5F is a perspective view of a rigid spacer, FIG. 5G is a perspective view of support structure for a plurality of rigid spacers, FIG. 5H is a top view of a central portion of an outlet fluid manifold, FIG. 5I is a top view of an upper portion of an outlet fluid manifold, and 5J is a perspective view of a system support rod;

FIGS. 7A–7B illustrate yet another alternative exemplary embodiment of a treatment chamber, wherein FIG. 7A is a top plan view of the treatment chamber, and FIG. 7B is a perspective view of the components of the treatment chamber prior to manufacture of the chamber.

DETAILED DESCRIPTION OF THE INVENTION

Figure 1A:
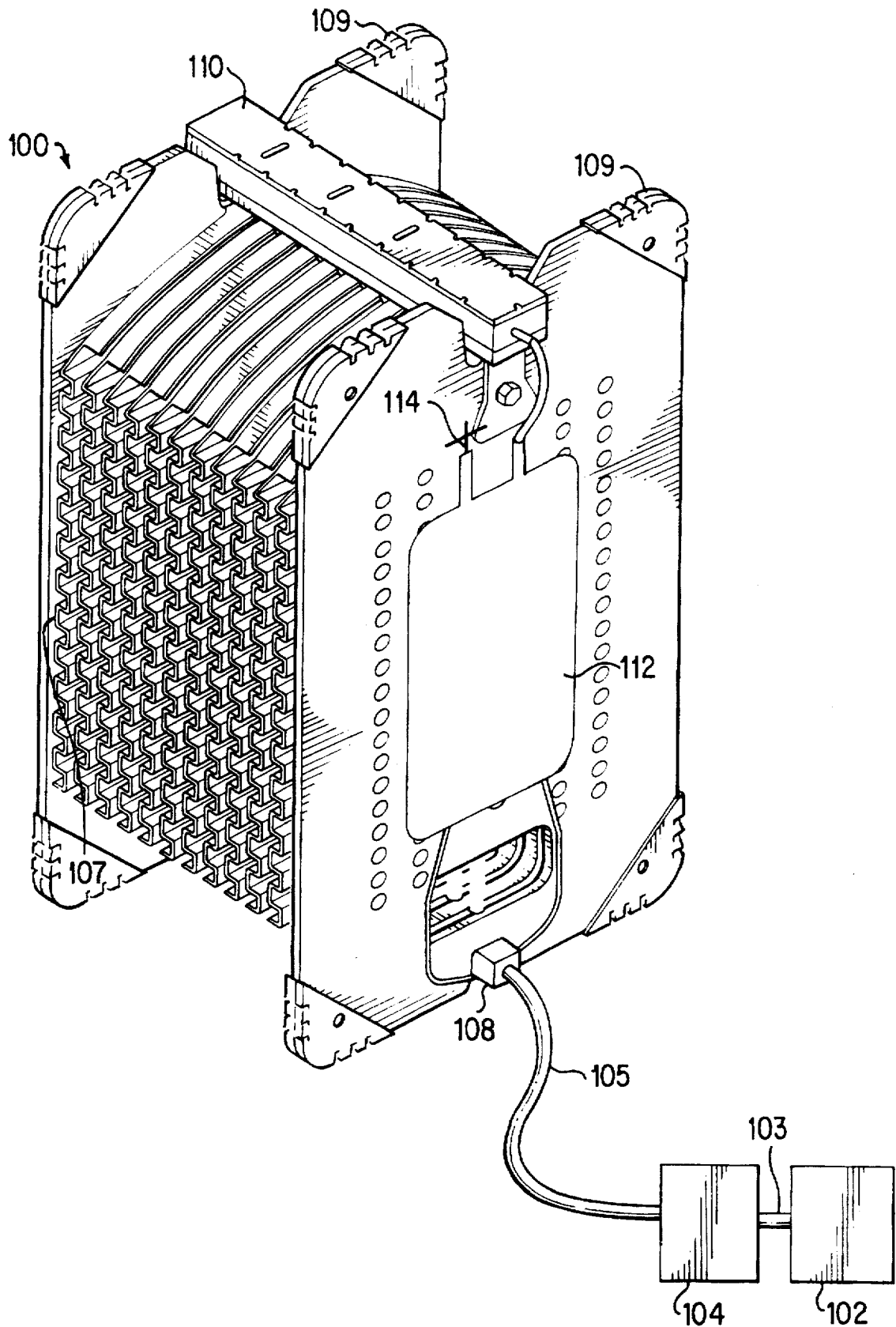

The following embodiments of the present invention will be described in the context of an apparatus for the large scale growth and packaging of cell suspensions and three-dimensional tissues, although those skilled in the art will recognize that the disclosed methods and structures are readily adaptable for broader application. Note that whenever the same reference numeral is repeated with respect to different figures, it refers to the corresponding structure in each such figure.

In accordance with the present invention, multiple treatment chambers are manifolded together during growth and culturing of transplants. These treatment chambers are advantageously flexible so as to provide for gas permeability and easy end-user handling during rinsing and application of the cultured transplants. However, flexible treatment chambers are not ideal for maintaining a constant culturing environment within the chambers during treatment. For example, if a vertical chamber orientation is utilized during treatment so as to facilitate the removal of potentially disruptive air bubbles away from the enclosed transplants, the flexible chambers will tend to bulge at the bottom. This distortion of the chambers during treatment creates an irregular and uneven culturing environment for the transplants. In addition, the distortion of the chamber can alter the surface area for oxygen transfer of the expansive, gas-permeable chambers, further compromising uniform production of cells and tissue for a given volume of media.

Accordingly, rigid spacers are provided which may be adapted to ensure even fluid distribution within the chambers during treatment. More particularly, proper fluid distribution is maintained by positioning each treatment chamber within the system between the rigid spacers in a configuration that ensures that fluid within each chamber is evenly distributed in much the same manner as would occur with the use of properly formed and defined rigid chambers.

In accordance with the foregoing, FIGS. 1A–1D disclose a system 100 for the large scale culturing and packaging of biological systems such as cell suspensions and three dimensional tissues. According to a first embodiment of the invention, this system primarily comprises a plurality of treatment chambers 106, a plurality of rigid spacers 107, an inlet fluid manifold 108, and an outlet fluid manifold 110 connected to both an overflow bag 112 and a vent filter 114, a fluid reservoir 102, and a means for transporting fluid from the fluid reservoir to the treatment chambers such as pump 104.

Fluid reservoir 102 is used to store fluid for the system. An illustrative suitable reservoir is any flexible 1L media bag, although one skilled in the art will understand that any fluid container capable of sterilization may be utilized. Examples of fluid which may be used in the system include, but are not limited to, fluid containing cells, fluid containing a culture medium, and fluids comprising various freezing solutions. It is to be understood that during culturing, the fluid may be advantageously kept at human body temperature.

The fluid contained in reservoir 102 is retrieved through fluid line 103 by a fluid delivery method such as pump 104. Although pump 104 is used herein in describing the structure and function of the invention, it is to be understood that other suitable means for transporting fluid would also fall within the scope of the invention. For example, fluid may be forced out of reservoir 102 and into fluid line 103 through the use of a common source of compressed gas, such as a house supply of clean, compressed nitrogen. Alternatively, fluid may be transported by gravity feed from a fluid reservoir placed at a higher elevation than the treatment chambers and manifolds themselves.

Fluid line 103, as well as all other fluid lines in the system, may be made of any type of sterilizable, durable tubing suitable for transporting the fluid in use. Pump 104 may be preferably any fluid pump which can achieve variable and bi-directional flow rates. One such pump is the Masterflex L/S Digital Drive peristaltic pump manufactured by Cole-Palmer, although one skilled in the art could select from a variety of commercially available pumps. Pump 104 propels the fluid from reservoir 102 to inlet fluid manifold 108 through fluid line 105.

Figure 1B:
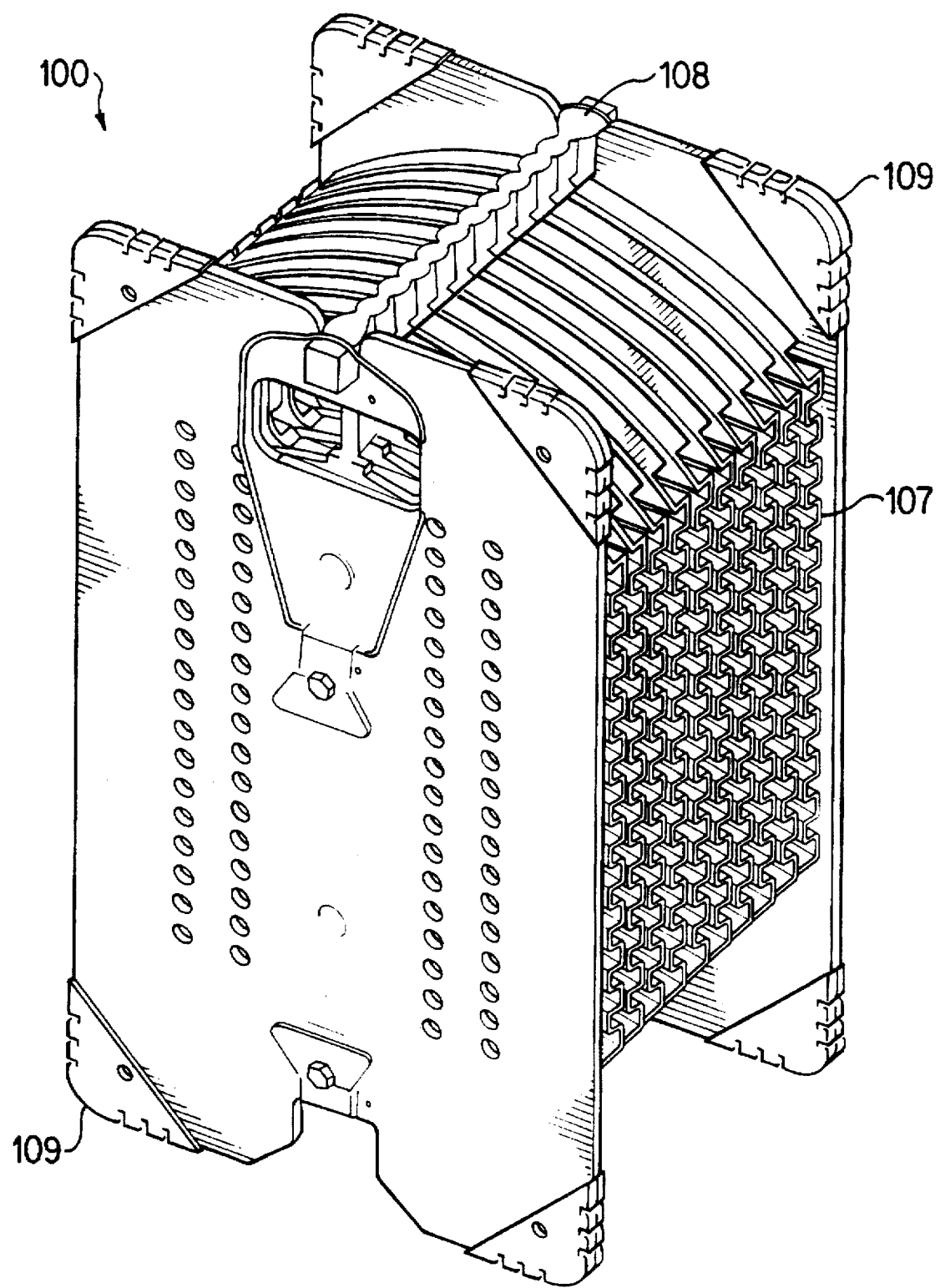
Figure 1C:
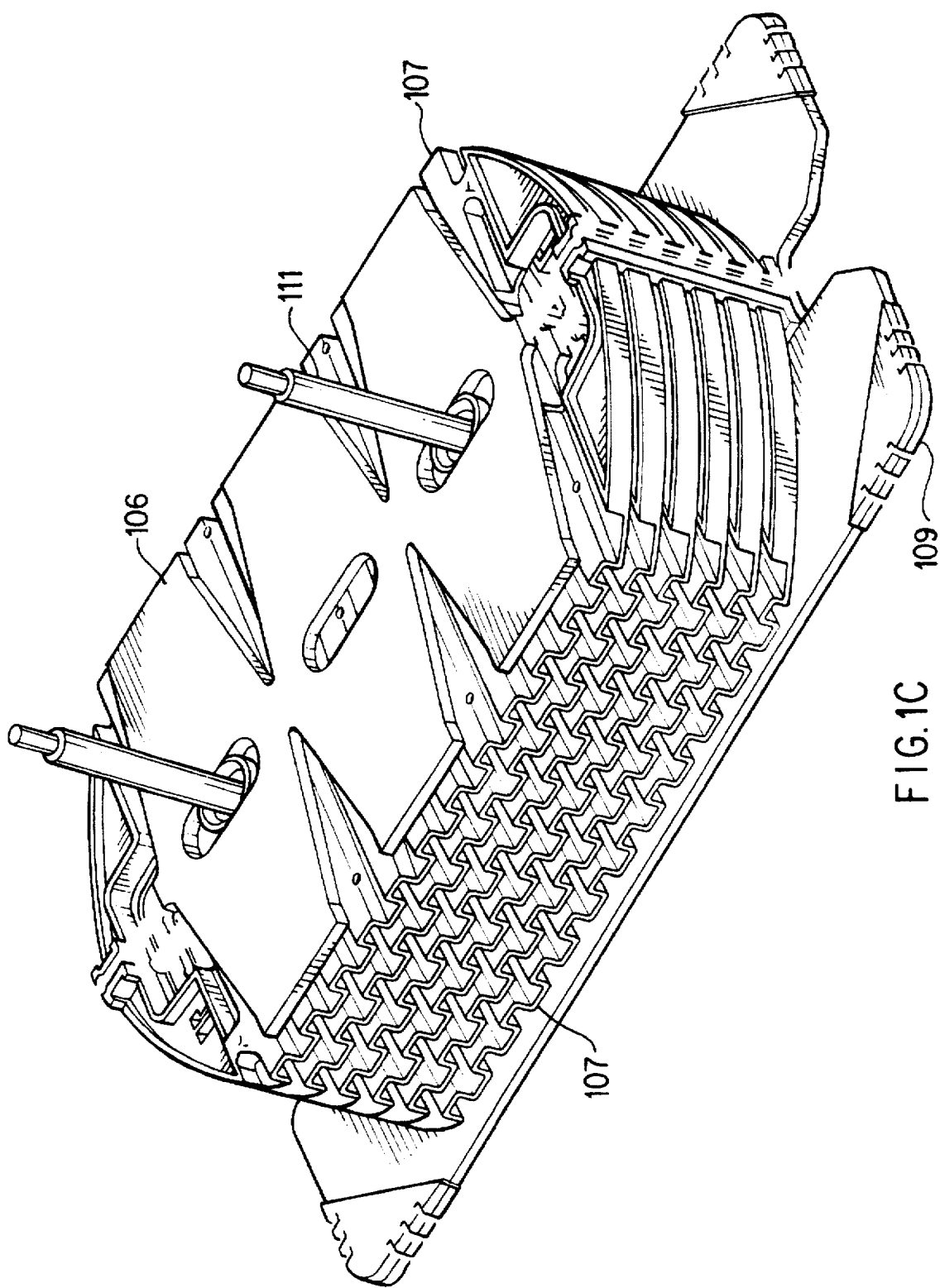

As shown in FIGS. 1A–1C, multiple treatment chambers 106 may be manifolded together utilizing inlet fluid manifold 108. The internal surfaces of inlet fluid manifold 108 can be advantageously angled and configured so as to ensure that any air bubbles entering the manifold are not trapped within the manifold itself. In order to ensure proper distribution of fluids into the multiple treatment chambers 106 when filling the same, system 100 should be oriented vertically such that the inlet manifold 108 is directly below treatment chambers 106 and outlet manifold 110. When system 100 is oriented in this manner, gravity will ensure that the fluid within the system equilibrates among the multiple interconnected treatment chambers.

As shown in FIG. 2A, a small length of narrow diameter tubing 202 at the inlet of treatment chambers 106 may be used within the system. If the system is to be operated in a continuous fluid circulation mode by connecting the outlet manifold 110 back to fluid reservoir 102, this narrow tubing 202 is advantageous as it will create a pressure drop between each treatment chamber and the inlet manifold 108. The pressure drop will further ensure proper fluid distribution within chambers 106 during treatment. In this continuous fluid circulation mode, the optimum diameter and tolerances for tubing 202 will depend at least in part upon the actual fluid flow rate used during treatment and upon the dimensions of inlet manifold 108.

FIGS. 2A–2B illustrate a first embodiment of a treatment chamber 106 which may be manifolded together in system 100. As shown in FIGS. 2A–2B, treatment chambers 106 include both an inlet port 202 and an outlet port 204.

Treatment chambers 106 may also be configured and dimensioned to house multiple tissue scaffolds 206. Tissue scaffolds 206 are preferably comprised of any biocompatible mesh material. Suitable materials include Vicryl™, which is produced by Ethicon, Inc., Somerville, N.J., and polyglycolic acid (PGA) mesh, which is produced by Albany International, Mansfield, Mass. and Davis & Geck, Danbury, Conn. Scaffolds 206 may be spot welded or bar welded within treatment chamber 106 at their corners (points A in FIG. 2A) so as to ensure the mesh will be held in place during treatment. Alternatively, scaffolds 206 may be sandwiched between welds during production of the treatment chamber itself, or welded or stitched to a rigid or semi-rigid frame, which could then be welded to the treatment chamber or simply confined within the treatment chamber by the outer weld demarcating each individual culture pocket. Especially for thinner tissue scaffolds, anchorage of the scaffold to the chamber is important during treatment to resist contractile forces which could cause the tissue to bunch or curl upon itself.

In addition to the bioabsorbable Vicryl™ and PGA meshes, scaffolds 206 may also be comprised of a nylon and silicone rubber combination such as Biobrane™, which is produced by Dow-Hickam. These silicone rubber membranes may serve as an artificial epidermis in use, and only require a growth system in which media contacts one side of the membrane. Therefore, when using Biobrane™ material in treatment chamber 106, spot welding need not be performed as the Biobrane™ material can be placed directly on the inside surface chamber and will maintain proper positioning due to electrostatic and hydrophobic forces.

Although only PGA mesh, Vicryl™ mesh, and Biobrane™ have been disclosed, one skilled in the art will understand that other mesh types and support structures are possible within the scope of this invention. In addition, although FIGS. 2A and 2B illustrate chamber 106 housing only six scaffolds 206, one skilled in the art will understand that any number of scaffolds 206 may be housed in treatment chamber 106. It is to be additionally understood that for certain cell-based therapies, no scaffolding may be required.

As illustrated in FIG. 2B, treatment chamber 106 may be manufactured by welding two pieces of film 210 together in a predetermined pattern. Film 210 must be biocompatible and must be able to maintain structural and compositional integrity under the sterilization/cultivation and freeze/thaw cycles which will be described in more detail below. In short, film 210 must be able to withstand irradiation, chemical, or thermal treatments to sterilize the treatment chambers 106 prior to culturing. In addition, the film 210 should preferably withstand freezing and storage at temperatures under −70° C., which is required to preserve the cultured cells or tissue, as well as subsequent thawing to room or body temperature once the cells or tissue are required for use. As a stagnant fluid system can be employed during culturing, film 210 should also be gas permeable so as to support tissue growth. In addition, film 210 must be amenable to reliable and readily available sealing and welding methods, which include heat, RF, and ultrasonic welding.

Any flexible materials which meet the above-specified requirements may preferably be considered for construction of treatment chambers 106. As mentioned previously, the plurality of treatment chambers may be advantageously flexible so as to provide for easy end-user handling during rinsing and application of the cultured transplants. Examples of acceptable flexible materials include polyolefins, polyolefin co-polymers, EVA and EVA copolymer blends, Exact®, PVC, PTFE, FEP, high density polyolefins, and thermoformed plastics, with EVA and EVA copolymer blends being most preferable due to the low cost, ease of fabrication, and optical clarity.

To ensure proper growth and culturing of the tissue, treatment chambers 106 should be formed in such a manner that ensures air bubbles do not lodge near scaffolds 206. A preferred pattern, shown in FIGS. 2A and 2B, containing angled sides (preferably >=5 degrees) along culture pockets 210, along with a vertical orientation during culturing (a horizontal orientation may also be used, and would also fall within the scope of the invention, but is not the preferred means of treatment), will ensure that any potentially disruptive air bubbles contained in the culturing fluid will be guided toward channel 212 and outlet port 204, and thus away from culture pockets 210 and tissue scaffolds 206.

Treatment chambers 106 may additionally include welded islands 214 in flow channel 212. These islands 214 are advantageous as they reduce the amount of welding which must be performed to separate the culture pockets 210 into individual storage chambers after treatment. Islands 214 are also advantageous as they provide an opening for support rods 111 (as depicted in FIG. 1C) and prevent fluid from simply channeling up the center of the treatment chamber (i.e., fluid is directed into the side culture pockets). Point B in FIG. 2A indicates where the post-treatment welding preferably occurs, and thus indicates the savings in post-treatment welding provided by islands 214.

As mentioned, vertical orientation during treatment will assist in moving potentially disruptive air bubbles away from scaffolds 206. However, vertical orientation also forces fluid to accumulate near the bottom of the flexible, expansive chambers 106. Proper fluid volume and distribution is therefore advantageously maintained by positioning each treatment chamber 106 between rigid spacers 107. Rigid spacers 107 may be corrugated as shown in FIGS. 1A–1C, or may contain perforations, as shown in FIG. 1D, so that adequate gas and heat transfer may occur while still maintaining even fluid distribution within the treatment chambers.

The positioning of chambers 106 between spacers 107 is additionally advantageous in that it will minimize contact between the chambers themselves, and between the chambers and personnel overseeing the cell or tissue treatment. Minimization of contact is preferable as such contact can result in damage to the treatment chambers and/or expose personnel to the potentially harmful contents of the treatment chambers.

As shown in FIGS. 1A–1C, a number of treatment chambers 106 and spacers 107 may be supported by end plates 109 and rods 111 which provide the structural stability and rigidity required for the precise application of force required to achieve a predetermined fluid distribution and volume in each treatment chamber. The combination of end plates, rods, and spacers is additionally beneficial as it provides a rigid structure which protects the flexible treatment chambers from accidental rupture during processing, thus promoting aseptic and safe culture of the cells or tissue. End plates 109, like spacers 107, may be perforated or corrugated to ensure adequate gas and heat transfer in the treatment chambers positioned directly against the end plates during use. Spacers 107, end plates 109, and rods 111 may be comprised of any rigid, durable material such as styrene, aluminum, magnesium, polycarbonate, Teflon, PVC, high density polyolefins, or stainless steel.

In an alternative embodiment, end plates 109 and rods 111 are not utilized as the means for ensuring structural integrity. In this alternative embodiment, spacers 107 need simply be attached to inlet manifold 108 and outlet manifold 110 in any manner known in the mechanical arts which would ensure structural integrity similar to that seen with the use of the combination of rods and end plates.

Once all treatment chambers 106 have been filled with fluid from reservoir 102 during use, fluid will exit chambers 106 through outlet ports 204 into outlet fluid manifold 110. Outlet fluid manifold 110 may be connected to an overflow bag 112 and/or an air filter 114 so as to provide for the removal of excess air and fluid from the system. Like fluid reservoir 102, overflow bag 112 may illustratively comprise a flexible plastic 1L media bag, although one skilled in the art will understand that any container capable of sterilization may be utilized.

Alternatively, and as previously mentioned, system 100 may include only one fluid reservoir which functions as both the reservoir from which fluid may be retrieved as well as the reservoir to which fluid may be dispensed. In this configuration, once the fluid media is ready to be removed from the system, fluid may be dispensed to the fluid reservoir simply by reversing pump direction, or alternatively, utilizing gravity to drain the fluid from the system. This single-reservoir configuration advantageously provides a closed, aseptic, and compact culturing environment. Outlet manifold 110 may also be connected to air filter 114 which facilitates the removal of unwanted air bubbles from the system during treatment and which facilitates the even and rapid filling of the treatment chambers 106.

Seeding and culturing of cell suspensions and three dimensional tissue in treatment chambers 106 is generally accomplished by known techniques, with the added benefits and advantages gained from the novel large scale culturing systems disclosed herein. Examples of suitable seeding and culturing methods for the growth of three-dimensional cell cultures are disclosed in U.S. Pat. No. 5,266,480, which is incorporated herein by reference. The techniques described in U.S. Pat. No. 5,266,480 for establishing a three-dimensional matrix, inoculating the matrix with the desired cells, and maintaining the culture may also be readily adapted by a person of ordinary skill in the art for use with the present invention. Known techniques for the culturing of cell suspensions for cell-based or gene-based therapies may also be readily adapted for use with the present invention.

Once all treatment chambers have been filled with the appropriate seeding and culturing medium in accordance with the structure described herein, and in accordance with known seeding and culturing techniques, tubing connecting upper manifold 110 to overflow bag 112, the overflow bag 112 to the vent filter 114, and tubing 105 connecting inlet manifold 108 and pump 104 may be clamped shut.

Once this tubing is clamped shut, system 100 may be rotated about one of its axes so as to maintain the suspension of cells during the culture of cell suspensions, and so as to ensure uniform seeding of tissue scaffolds during the culture of the same. In the case of tissue culture, once the tissue scaffolds have been uniformly seeded, the system can, but need not be rotated for the remainder of the culturing process.

During the seeding and culturing of cells and tissue, system 100 may be advantageously placed in a controlled environment enclosure, in which environmental parameters such as temperature, as well as oxygen and carbon dioxide concentrations, may be controlled as necessary to achieve desired growth conditions.

Once the tissue scaffolds have reached the desired level of cell density, the culture medium may be pumped out of the system and replaced with a freezing solution so as to facilitate cryopreservation of the tissue. When the treatment chambers have been filled with the freezing solution, the inlet ports 202 and outlet ports 204 of the treatment chambers may then be sealed so as to create a sealed chamber which may then be removed from system 100.

In the case of cell suspension cultures which do not require scaffolding, treatment chambers 106 containing the cell suspensions may not require the introduction of a freezing solution and may be simply sealed shut.

Once sealed treatment chambers 106 have been removed from system 100, individual culture pockets 210 may then be sealed and separated as explained above. These individual pockets can be sealed through any of the established welding methods mentioned above, and separated through the use of a known die-cutting operation or through the use of tear seals. The individual pockets may then be frozen using conventional freezing methods, or, alternatively, the entire multiple-piece chamber may be frozen as one unit, depending upon the clinical application. In this manner, sealed treatment chambers 106 may be used to culture, store, and ship cells, tissue cultures, and other biological systems.

FIGS. 3A–3D disclose an alternative exemplary embodiment of a system for the large scale culturing and packaging of cell suspensions and three dimensional tissue. Alternative embodiment 300 primarily comprises a fluid reservoir 102, a pump 104, a plurality of treatment chambers 106, a plurality of spacers 306, an inlet fluid manifold 312, an outlet fluid manifold 314, an overflow bag (which may be embedded in end plate 310), and a vent filter 315.

Fluid reservoir 102 and pump 104 function in the same manner as those described in conjunction with FIGS. 1A–1D above. In particular, reservoir 102 is used to store fluid for the system, while pump 104 is used to provide fluid to and retrieve fluid from the system. As mentioned, although pump 104 is used herein in describing the structure and function of present invention, it is to be understood that other suitable means for transporting fluid would also fall within the scope of the present invention.

Figure 3A:
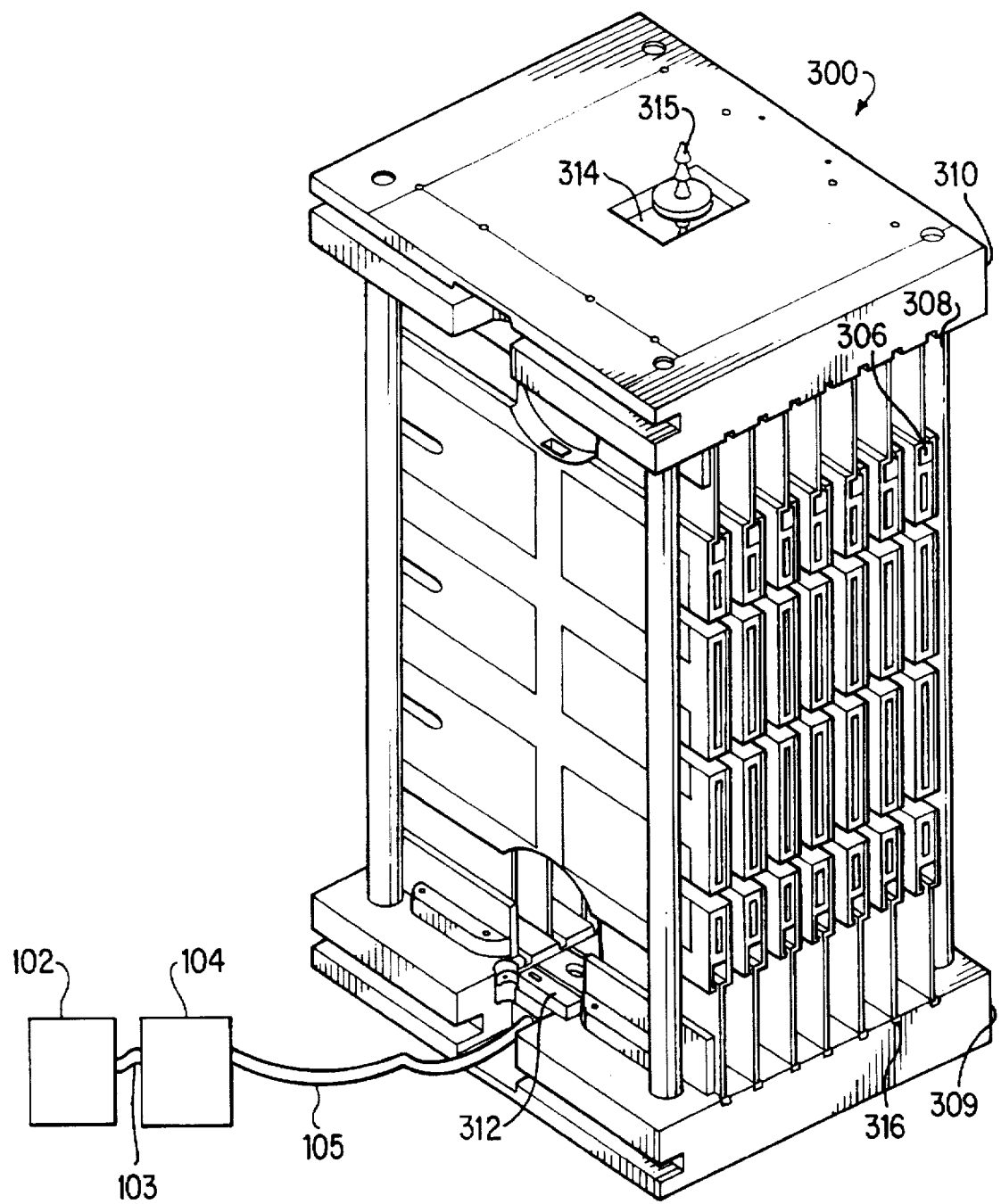
Figure 3B:
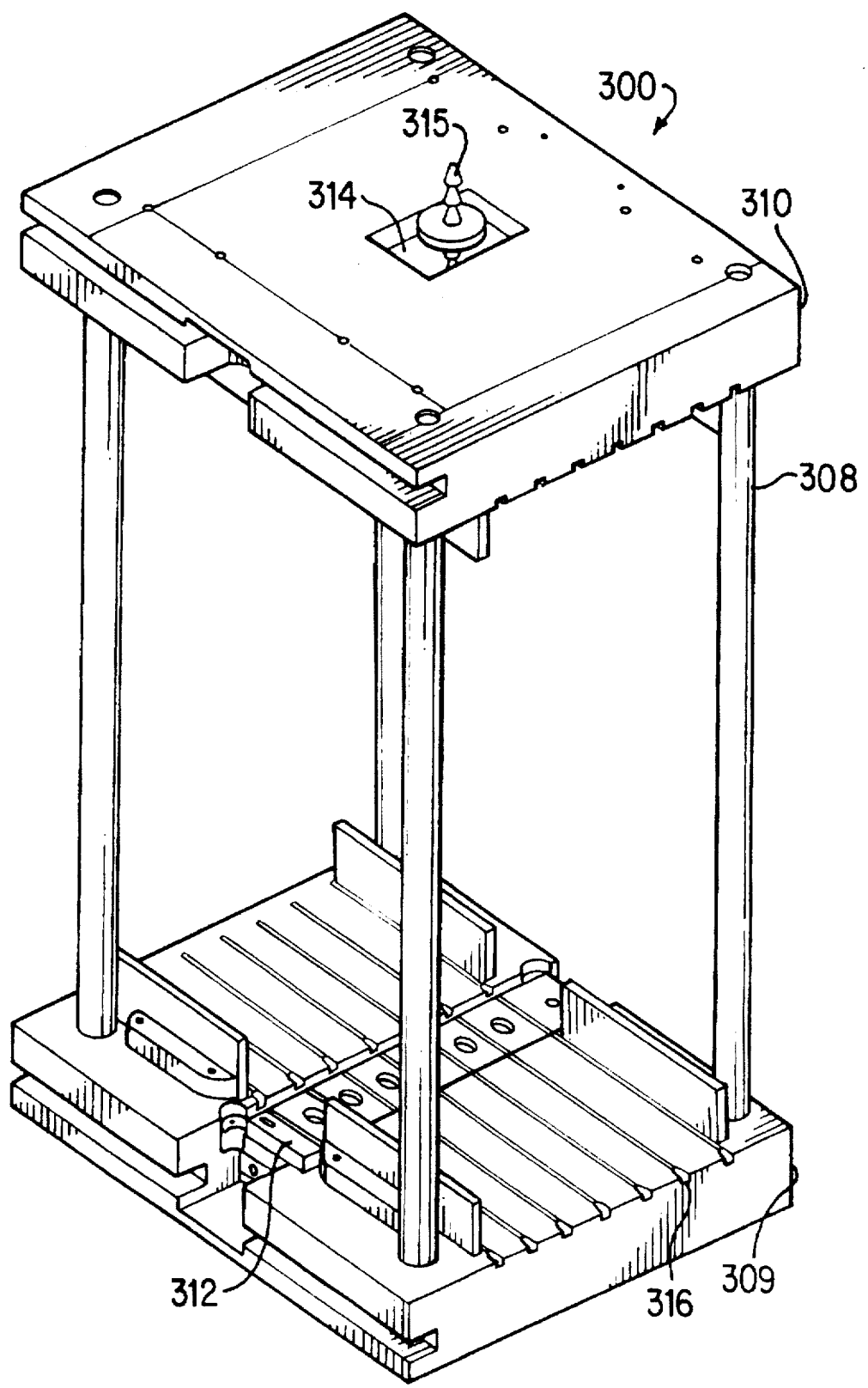
Figure 3C:
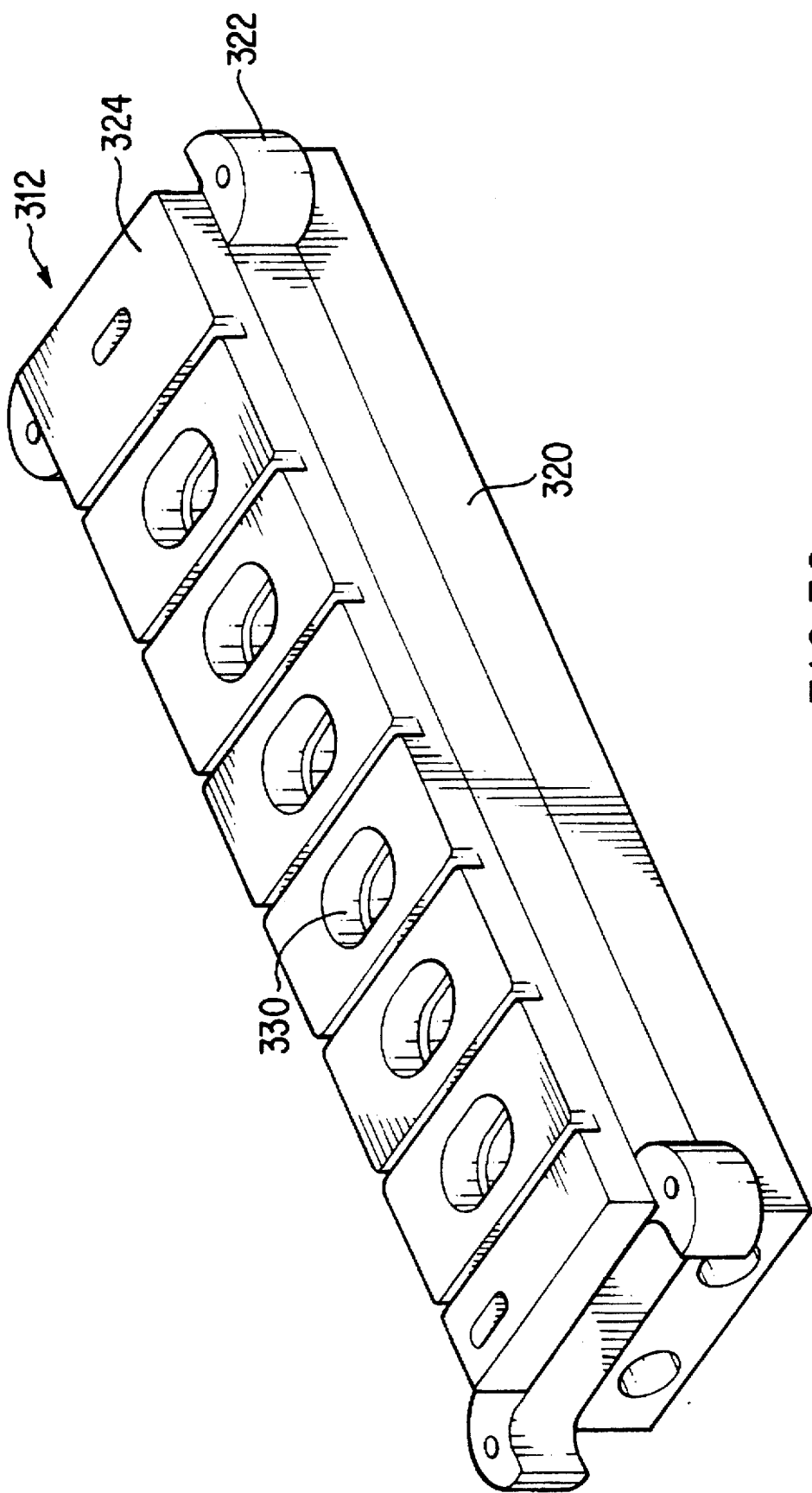
Figure 4A:
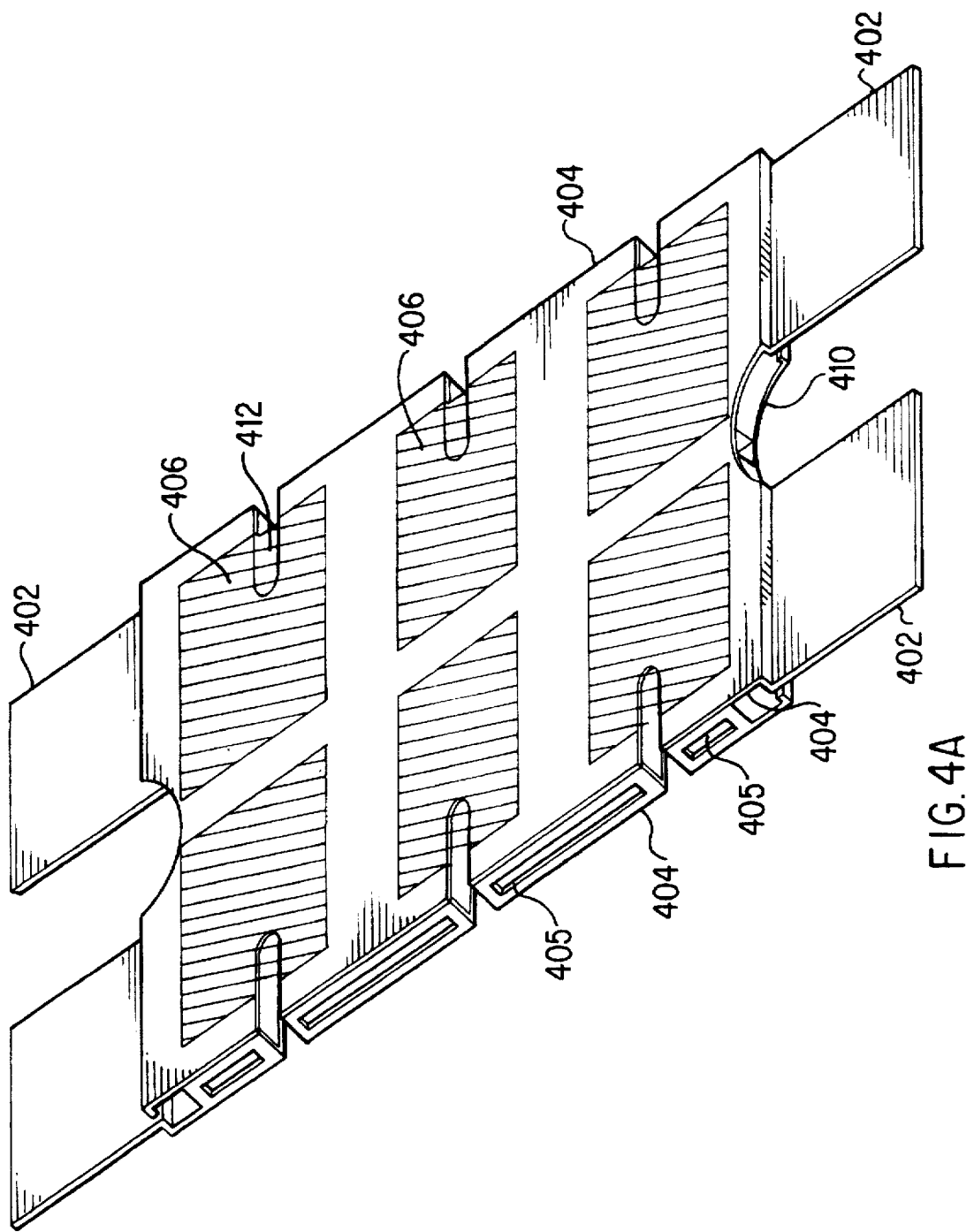

As shown in FIG. 3A, inlet fluid manifold 312 may be used to manifold together multiple treatment chambers 106 (not shown in FIG. 3A), which are described in conjunction with FIGS. 2A–2B above. Inlet fluid manifold 312 is illustrated more particularly in FIGS. 3C and 3D. As shown in FIGS. 3C and 3D, inlet fluid manifold may be comprised of a lock plate 324, a connector plate 322, and a fluid inlet piece 320. Lock plate 324 may be used to secure tubing 202 of the growth chambers to the fluid manifold. Specifically, tubing 202 may fit securely within one of the plurality of openings 330 in connector plate 322. Connector plate 322 functions to secure the fluid manifold 312 to end plate 309 as shown in FIGS. 3A and 3B. Fluid inlet piece 320 includes a longitudinally extending fluid channel 321 and fluid inputs 323 so as to facilitate the flow of fluid from the fluid reservoir to each opening 330 and thus each treatment chamber 106 in the system. Fluid channel 321 is preferably configured so as to ensure that no air bubbles become trapped in the manifold itself.

As shown in FIGS. 3A–3B, treatment chambers 106 and rigid spacers 306 may be supported by rods 308 in conjunction with end plates 309 and 310. This combination of end plates and rods provides the structural stability and rigidity required for the precise application of force to treatment chambers 106 to achieve a predetermined fluid distribution in each chamber during treatment. More particularly, the vertical orientation of chambers 106 during treatment gravitationally forces fluid within the flexible chamber to accumulate near the bottom of such chambers. Accordingly, proper fluid distribution of fluid is advantageously maintained by positioning each treatment chamber 106 between rigid spacers 306 which are in turn stabilized by the combination of end plates 309 and 310 along with rods 308.

FIGS. 4A–4D disclose an exemplary embodiment of rigid spacers 306. As shown in FIGS. 4A–4D, spacers 306 include sections 402 for slidably mating with slots 316 of end plates 309 and 310. Sections 402 preferably include a smooth outer surface so as to facilitate this mating. Spacers 306 also include a central area comprised of two flat surfaces 404 attached by edge pieces 405. Edge pieces 405 rigidly support a predetermined width between surfaces 404. Surfaces 404 may also include semi-circular sections 410 which allow for easy access to chamber tubing 202 and 204 during use. This ease of access is advantageous for visual observation of fluid distribution and for welding of tubing 202 and 204 after treatment, but prior to disengagement from the system. In addition, surfaces 404 may also include open areas 412 which allow for various end user features on the treatment chambers such as side ports (shown in FIG. 2A).

Surfaces 404 may also include perforated areas 406 which, along with the spacing between surfaces 404, allow for adequate gas and heat transfer from chambers 106 during treatment, but do not compromise the maintenance of even fluid distribution within the chambers themselves. One example of a suitable perforation pattern is a 60° pattern with 50% open air and with holes less than 0.5 inches in diameter. However, one skilled in the art will understand that other perforation patterns are equally suitable and equally acceptable. These perforated areas 406 may be advantageously positioned in areas which will contact those regions of chambers 106 which are occupied by scaffolds 206 or cell suspensions. Spacers 306 may preferably be comprised of any rigid material such as stainless steel, Teflon®, or polycarbonate.

Once all treatment chambers 106 have been filled with fluid, fluid will exit chambers 106 through outlet port 204 into outlet fluid manifold 314. Outlet fluid manifold 314 may be connected, like outlet manifold 110 described in conjunction with FIGS. 1A–1D above, to an overflow bag (which may be embedded in end plate 310) and an air vent filter 315. Alternatively, system 300 may include only one fluid reservoir which functions as both the reservoir from which fluid may be retrieved as well as the reservoir to which fluid may be dispensed.

The seeding, culturing, freezing, and storage of cells or tissue scaffolds 206 in treatment chambers 106 is generally accomplished by the techniques described above in conjunction with system 100. In addition, during culture of cells or tissue, system 300, like system 100, may be advantageously placed in a controlled environment enclosure, in which environmental parameters such as temperature, as well as oxygen and carbon dioxide concentrations, may be controlled as necessary to achieve desired growth conditions.

FIGS. 5A–5J disclose yet another alternative exemplary embodiment of a system for the large scale culturing and packaging of cell suspensions and three dimensional tissue. According to this alternative embodiment 500 of the invention, the system primarily comprises a fluid reservoir 102, a pump 104, a plurality of treatment chambers 600, a plurality of spacers 512, an inlet fluid manifold 514, and an outlet fluid manifold 502 connected to a hydrophobic air filter 522. Fluid reservoir 102 and pump 104 function in the same manner as those described in conjunction with FIGS. 1A–1D above.

As shown in FIGS. 5A–5J, inlet fluid manifold 514 may be used to manifold together multiple treatment chambers 600, one exemplary embodiment of which is described in conjunction with FIG. 6 below. Inlet manifold 514 is comprised of a lock plate 508, a center portion 518, and a bottom portion 520. Center portion 518 and bottom portion 520 form the manifold fluid channels, while lock plate 508 may be configured and adapted to secure the treatment chamber inlet ports to the manifold itself. In addition, an o-ring may be placed in groove 535 (shown in FIG. 5C) so as to create a sealed manifold chamber.

Fluid from pump 104 and fluid line 105 may enter inlet manifold 514 through inlets 533. Alternatively one inlet may be used as an inlet, while the other may be used as an outlet so as to drain fluid from the system. From inlet 533, fluid may pass to multiple apertures 530 and 532 (shown in FIGS. 5D and 5E) through channels 534 (shown in FIG. 5C). In this fashion, fluid may be evenly distributed from the fluid reservoir 102 to each of the attached treatment chambers 600.

As previously discussed, the vertical orientation of the treatment chambers during treatment gravitationally forces fluid within the flexible chamber to accumulate near the bottom of such chambers. Accordingly, proper even distribution of fluid is advantageously maintained by positioning each treatment chamber between rigid spacers 512 which are in turn stabilized by spacer supports 510.

Figure 5A:
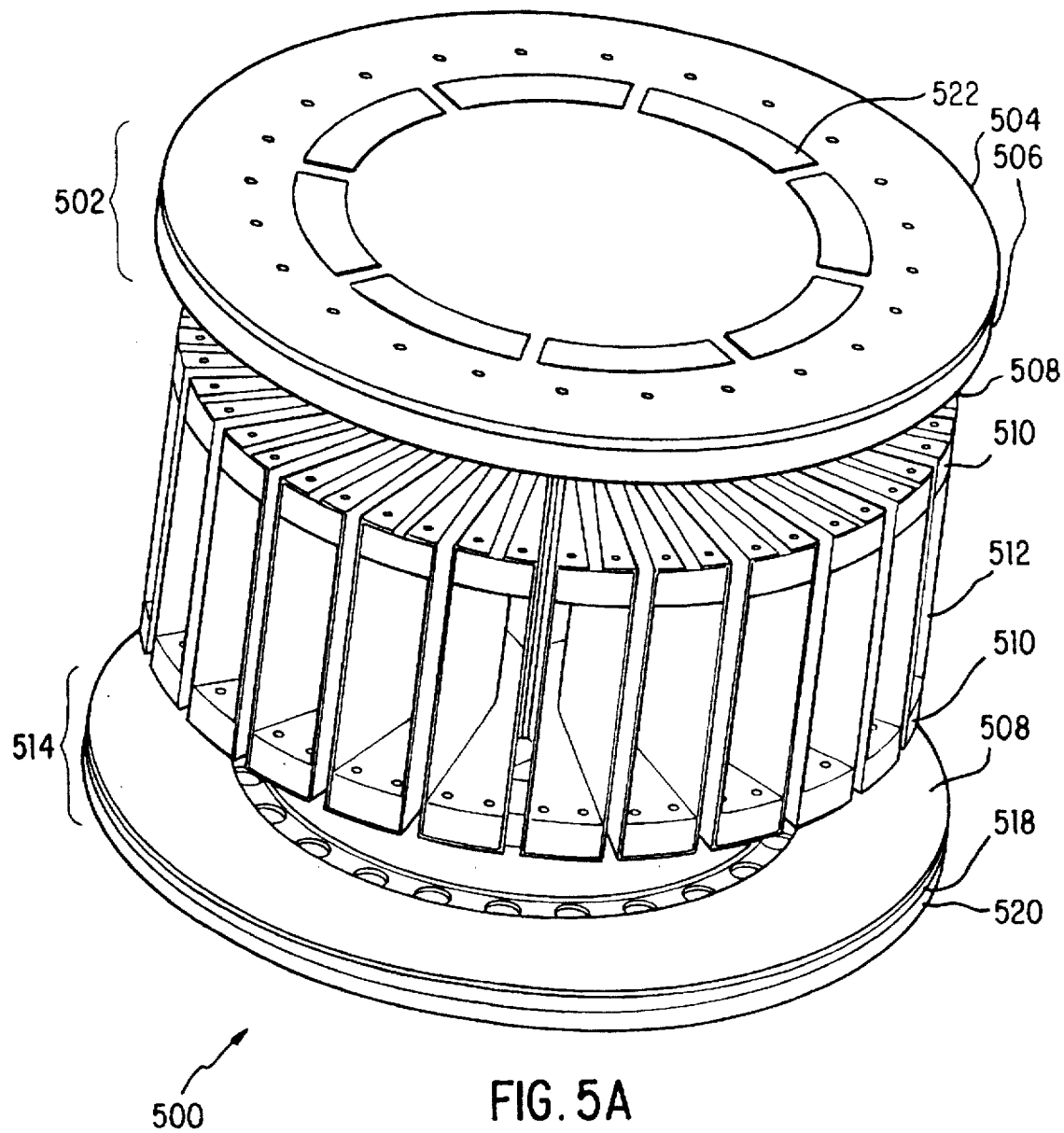
Figure 5B:
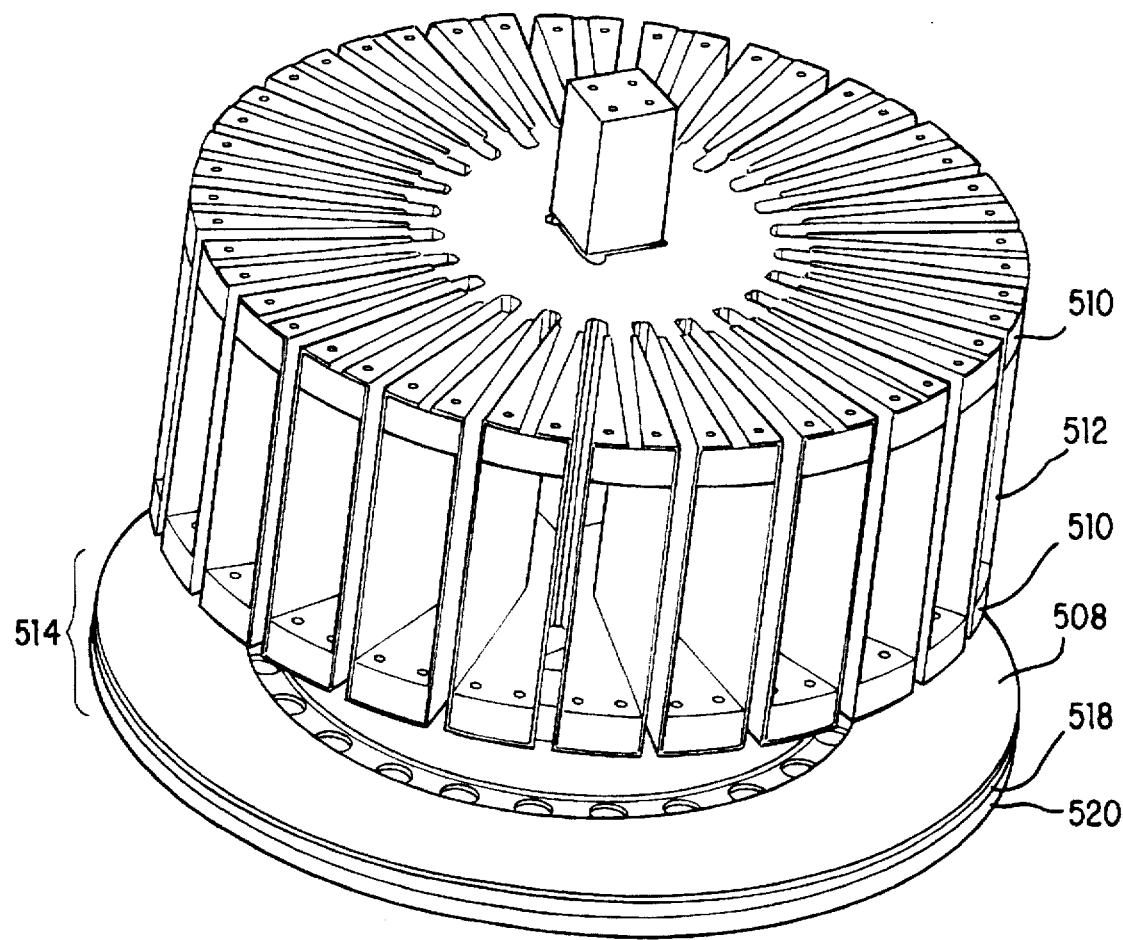
Figure 5C:
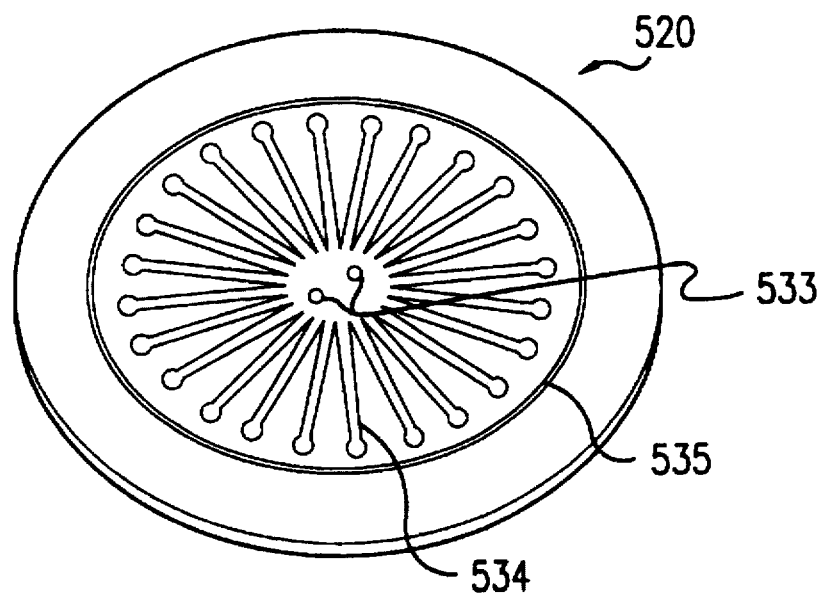
Figure 5D:
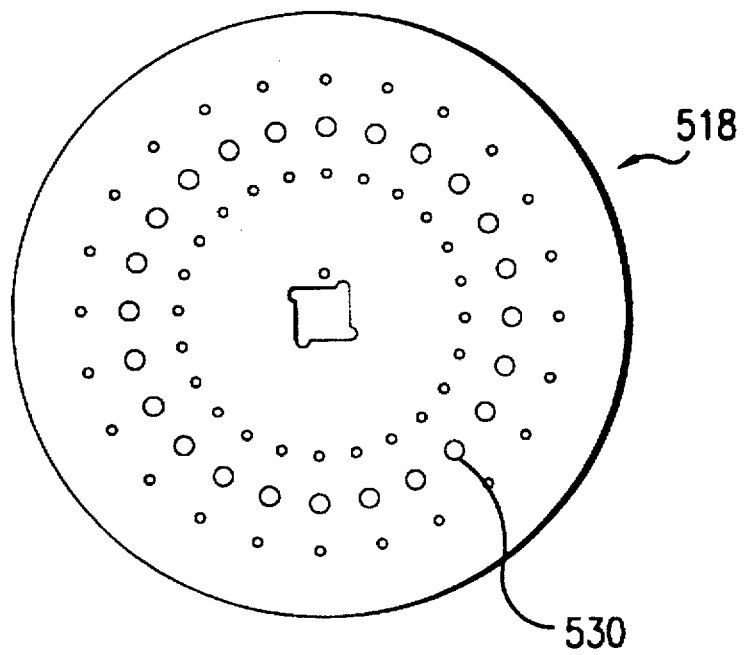
Figure 5E:
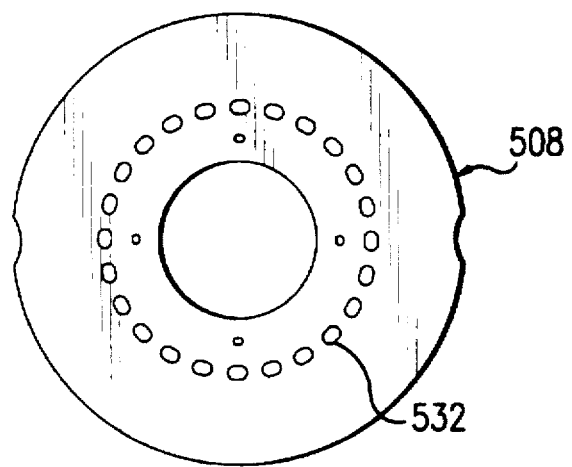
Figure 5F:
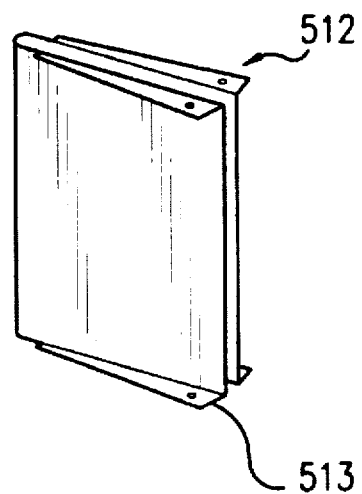
Figure 5G:
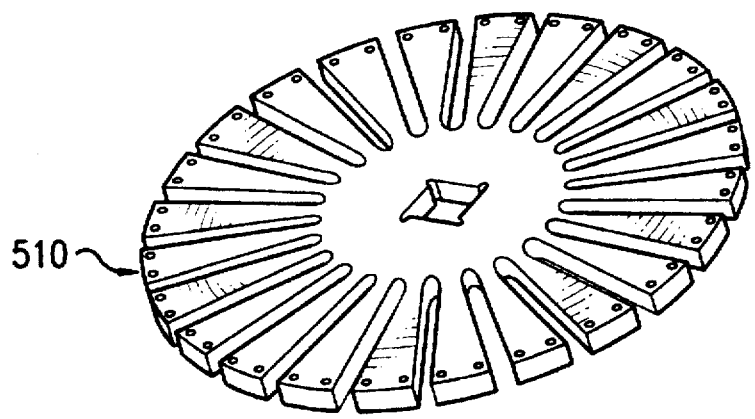
Figure 5H:
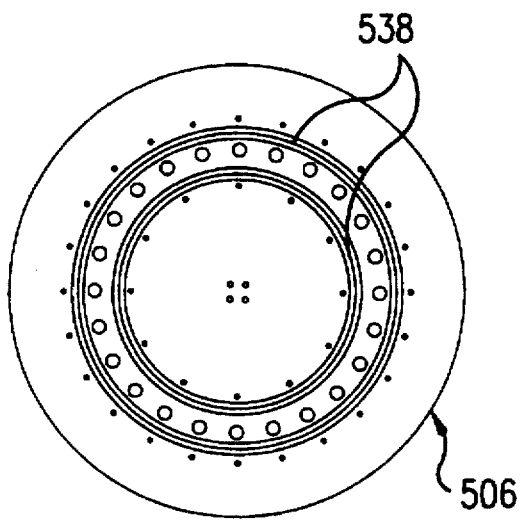
Figure 5I:
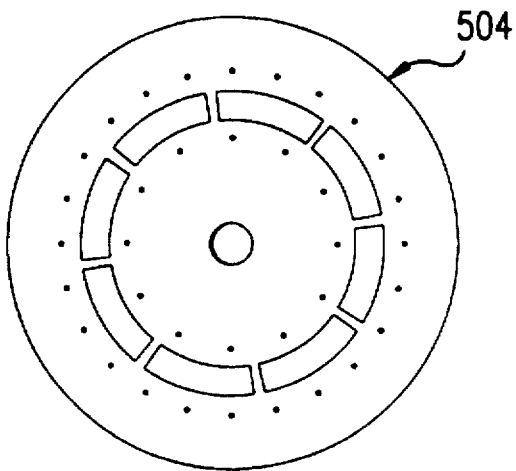

FIGS. 5F and 5G, respectively, disclose preferred embodiments of rigid spacers 512 and spacer supports 510. As shown in FIG. 5F, spacers 512 form a gap 513 of a predetermined width between two flat surfaces. It is within this formed gap 513 where treatment chambers 600 may be positioned so as to ensure proper fluid distribution during treatment. These spacer surfaces may also be corrugated or may include perforations which, along with the spacing between spacers 512, allow for adequate gas and heat transfer from treatment chambers 600 during treatment, but do not compromise the maintenance of even fluid distribution within the chambers. As mentioned, one example of a suitable perforation pattern is a 60° pattern with 50% open air and with holes less than 0.5 inches in diameter. However, one skilled in the art will understand that other perforation patterns are equally suitable and equally acceptable. These perforated areas may be advantageously positioned in regions of the spacers which will contact those areas of the chambers occupied by the tissue scaffolding or the cell suspensions. Spacers 512, along with the other components of system 500, may preferably be comprised of any rigid material such as stainless steel, Teflon®, or polycarbonate.

Once all treatment chambers 600 have been filled with fluid during treatment, fluid will exit the chambers through their outlet ports into outlet fluid manifold 502. Outlet fluid manifold 502 may be connected, like outlet manifold 110 described in conjunction with FIGS. 1A–1D above, to an overflow bag and an air vent filter. Alternatively, and as shown in FIG. 5A, system 500 may include only an air filter 522, which may be secured within outlet manifold 504. In yet another alternative embodiment, system 500 may include only one fluid reservoir which functions as both the reservoir from which fluid may be retrieved as well as the reservoir to which fluid may be dispensed.

Outlet manifold 502 may be comprised of a lock plate 508, a central portion 506, and an upper portion 504. Lock plate 508 allows for the firm attachment of the outlets of treatment chambers 600 to the outlet manifold, while central portion 506 and upper portion 504 form the fluid channels of manifold. In addition, an o-ring may be placed in grooves 538 so as to create a sealed outlet manifold chamber, which as mentioned above, may be used to house an air filter 522.

Figure 5J:
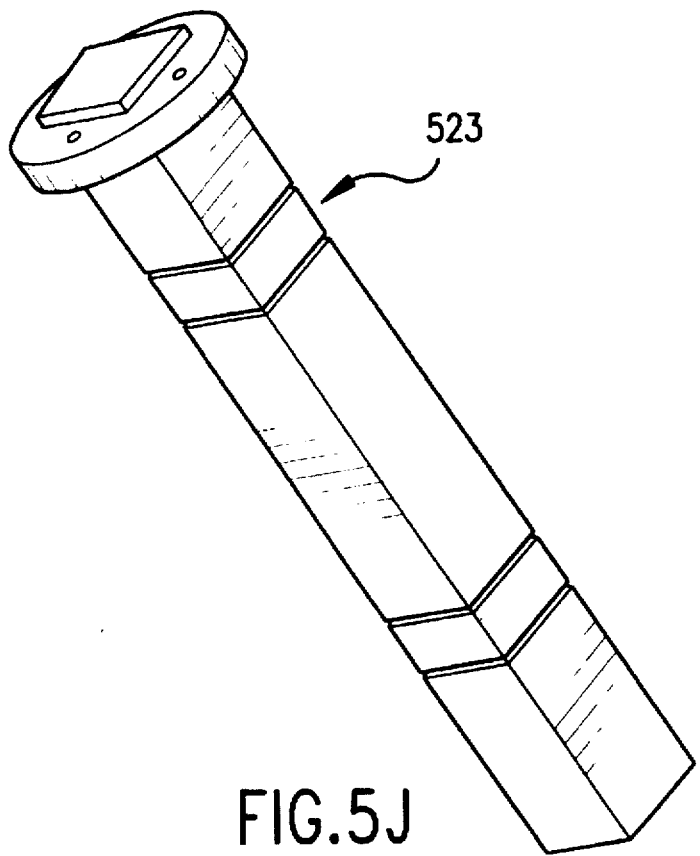

As also shown in FIGS. 5B and 5J, treatment chambers 600 and rigid spacers 512, along with the inlet and outlet manifolds, may be supported by a support rod 523. The combination of manifolds 502 and 514, along with rod 523, provides the structural stability and rigidity required for the precise application of force required to achieve a predetermined volume and distribution of fluid in each treatment chamber during treatment.

The seeding, culturing, freezing, and storage of the tissue scaffolds 206 in treatment chambers 600 within system 500 is generally accomplished by the techniques described above in conjunction with system 100. In addition, during culture of cells or tissue, system 500, like systems 100 and 300, may be advantageously placed in a controlled environment enclosure, in which environmental parameters such as temperature, as well as oxygen and carbon dioxide concentrations, may be controlled as necessary to achieve desired growth conditions.

Figure 6:
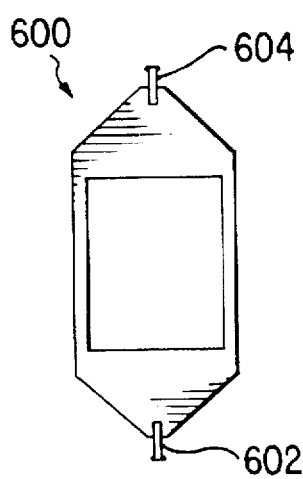
FIG. 6 is a top plan view of an alternative exemplary embodiment of a treatment chamber.

FIG. 6 illustrates yet another embodiment of a treatment chamber which may be utilized individually or may be manifolded together in systems such as systems 100, 300, and 500. As shown in FIG. 6, treatment chamber 600 may include both an inlet port 602 and an outlet port 604. Treatment chamber 600 may also be configured and dimensioned to house a tissue scaffold 206 such as described in conjunction with FIGS. 2A and 2B above. As also described above, scaffold 206 may, if necessary, be spot welded within the chamber 600 at its corners to ensure that the scaffolding remains in place during treatment. Alternatively, scaffold 206 may be sandwiched between welds during production of the treatment chamber itself, or welded or stitched to a rigid or semi-rigid frame, which could then be welded to the treatment chamber or simply confined within the treatment chamber by the outer weld demarcating each individual culture pocket.

Like treatment chamber 106, treatment chamber 600 may be manufactured by welding two pieces of flexible film together in a predetermined configuration. The film must be biocompatible and must be able to maintain structural and compositional integrity under the sterilization/cultivation and freeze/thaw cycles which were previously described in detail. Because a stagnant fluid system can be employed during culturing, film 210 should also be gas permeable to support tissue growth. In addition, film 210 must be amenable to reliable and readily available sealing and welding methods, which include heat, RF, and ultrasonic welding.

Any flexible materials which meet the above-specified requirements may preferably be considered for construction of chamber 600. As mentioned previously, the plurality of treatment chambers may be advantageously flexible so as to provide for easy end-user handling during rinsing and application of the cultured transplants. Examples of acceptable flexible materials include polyolefins, polyolefin co-polymers, EVA and EVA copolymer blends, Exact®, PVC, PTFE, FEP, high density polyolefins, and thermoformed plastics, with EVA and EVA copolymer blends being most preferable due to the low cost, ease of fabrication and optical clarity.

To ensure proper growth and culturing of the tissue, chamber 600 should be configured and dimensioned in such a manner that ensures air bubbles do not lodge near scaffolds 206 during treatment. The preferred pattern shown in FIG. 6 containing an angled top and bottom (preferably >=5 degrees), along with a vertical orientation during culturing, will ensure that any potentially harmful air bubbles contained in the culturing fluid will be guided toward outlet port 604, and thus away from tissue scaffolds 206.

Figure 7A:
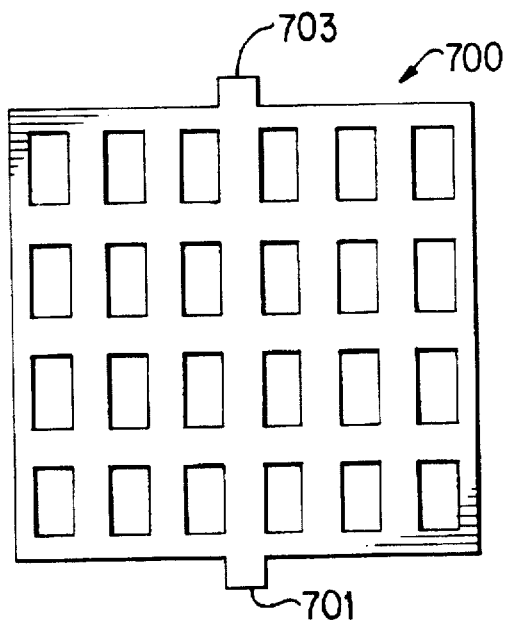
Figure 7B:
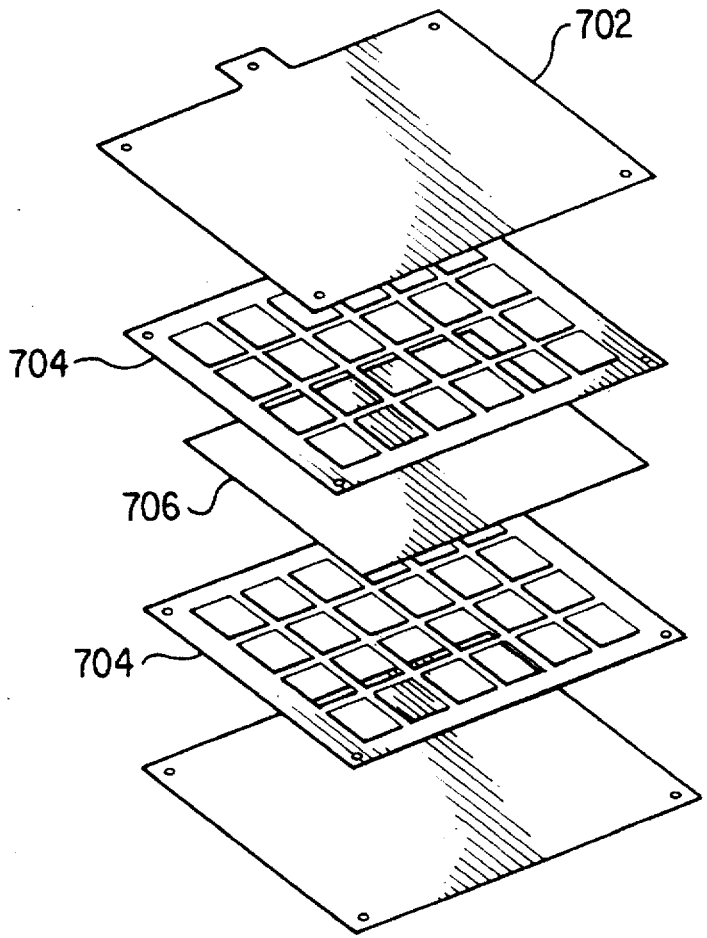

FIGS. 7A and 7B illustrate a third embodiment of a treatment chamber which may be utilized individually or may be manifolded together in systems such as systems 100, 300, and 500. As shown in FIGS. 7A and 7B, treatment chamber 700 may include both an inlet port 701 and an outlet port 703. However, if treatment chamber 700 is not to be used in a manifolded configuration such as systems 100 and 300, treatment chamber 700 need not include both inlet and outlet ports. Treatment chamber 700 may also be configured and dimensioned to house a tissue scaffold 706.

Tissue scaffold 706, like scaffold 206, is preferably comprised of any biocompatible mesh material. Suitable mesh materials include Vicryl™ mesh and polyglactin or PGA mesh. Especially for thinner tissue scaffolds, anchorage of the scaffold to the chamber is important during treatment to resist contractile forces which could cause the tissue to bunch or curl upon itself. Accordingly, scaffold 706 may be attached on either side to frames 704. Frames 704 may be configured in a grid pattern, as shown in FIGS. 7A and 7B, although one skilled in the art will understand that other patterns may be appropriate in various clinical situations. Scaffold 706 may be attached to frames 704 in any manner although established welding methods such as RF, ultrasonic, or heat welding are preferred.

In addition to the bioabsorbable Vicryl™ and PGA meshes, scaffold 706 may also be comprised of a nylon and silicone rubber combinations such as Biobrane™. Because Biobrane™ only requires a growth system in which media contacts one side of the membrane, and because it will maintain proper positioning due to electrostatic and hydrophobic forces, Biobrane™ material can be placed directly on the surface of frames 704. As mentioned previously, although only Biobrane, PGA mesh, and Vicryl™ mesh have been disclosed, one skilled in the art will understand that other tissue types and support structures are possible within the scope of this invention.

As shown in FIG. 7B, treatment chamber 700 may be manufactured by welding the framed scaffold 706 in between two pieces of film 702. Film 702 and frame 704 must be biocompatible and must be able to maintain structural and compositional integrity under the sterilization/cultivation and freeze/thaw cycles which were described in detail above. Because a stagnant fluid system can be employed during culturing, film 702 should also be gas permeable to support growth for the tissue. Finally, film 702 should be amenable to reliable and readily available sealing and welding methods.

Any materials which meet the above-specified requirements may preferably be considered for construction of chamber 700. Examples of acceptable materials include polyolefins, polyolefin co-polymers, EVA and EVA copolymer blends, Exact®, PVC, PTFE, FEP, high density polyolefins, and thermoformed plastics, with EVA and EVA copolymer blends being most preferable due to its low cost, ease of fabrication and optical clarity.

Various embodiments of the invention have been described herein. The descriptions are intended to be illustrative, not limitative. Thus, it will be apparent to those skilled in the art that modifications may be made to the invention as described without departing from the scope of the claims set out below.

What is claimed is:

1. An apparatus, comprising
   a plurality of growth chambers comprising flexible front and back sheets bonded together along predetermined boundaries to delimit a first port for the inflow of fluid into said growth chambers, a second port for the outflow of fluid from said growth chambers, and at least one compartment for growth of tissue;
   at least one substrate disposed within each of said plurality of growth chambers designed to facilitate three-dimensional tissue growth on said substrate;
   a plurality of spacer members adapted to contact the flexible growth chambers in a manner which maintains even fluid distribution within the chambers, thereby promoting even growth of tissue;
   an inlet manifold with an inlet port and a plurality of outlet ports for uniformly providing fluid to the growth chambers, said outlet ports adapted to mate with the first ports of the growth chambers;
   an outlet manifold with a plurality of inlet ports, each of said inlet ports adapted to mate with the second ports of the growth chambers; and
   a support member for connecting said plurality of spacer members to said inlet and outlet manifolds.

2. The apparatus of claim 1, wherein said growth chambers comprise:
   a plurality of growth compartments within said growth chambers, said growth compartments each configured and dimensioned to house a substrate; and
   an internal passageway fluidly connecting said plurality of growth compartments to said first and second ports.

3. The apparatus of claim 1, further comprising:
   a supply of fluid in fluid communication with the inlet port of the inlet manifold; and
   fluid transportation means for supplying the fluid to the inlet port of said inlet manifold.

4. The apparatus of claim 3, wherein the fluid transportation means comprises a fluid pump.

5. The apparatus of claim 1, further comprising a second support member configured and dimensioned to support and maintain a predetermined distance between said spacer members.

6. The apparatus of claim 1, wherein said spacer members are configured and dimensioned to support and maintain a predetermined distance between said members.

7. The apparatus of claim 1, wherein said inlet and outlet manifolds are configured and dimensioned to support and maintain a predetermined distance between said spacer members.

8. The apparatus of claim 1, wherein said support member comprises the spacer members and the inlet and outlet manifolds.

9. The apparatus of claim 1, wherein said support member is a rod for connecting said spacers to said inlet and outlet manifolds.

10. The apparatus of claim 1, wherein said outlet manifold further includes an air filter for removal of air from the apparatus during treatment.

11. The apparatus of claim 1, wherein said outlet manifold further includes an outlet port, said outlet port in fluid communication with an overflow container for accepting excess fluid entering said outlet manifold.

12. The apparatus of claim 3, wherein said outlet manifold includes an outlet port, said outlet port in fluid communication with said supply of fluid so as to create a closed fluid loop within the apparatus.

13. An apparatus for promoting the growth of tissue, comprising:
   a plurality of growth chambers defined by flexible front and back walls, said chambers each having a first port and a second port for flow of fluid therethrough;
   at least one substrate disposed within each of said plurality of growth chambers designed to facilitate three-dimensional tissue growth on said substrate;
   an inlet manifold with an inlet port and a plurality of outlet ports, each of said outlet ports in fluid communication with one of said first ports of said growth chambers;
   a supply of fluid in fluid communication with the inlet port of said inlet manifold;
   fluid transportation means for supplying fluid to the inlet port of said inlet manifold; and
   an outlet manifold with a plurality of inlet ports, each of said inlet ports in fluid communication with one of said second ports of said growth chambers.

14. The apparatus of claim 13, wherein each of said growth chambers further comprises:
   a plurality of growth compartments defined by said flexible front and back walls bonded together along predetermined boundaries; and
   an internal passageway fluidly connecting said plurality of growth cells, said passageway further connecting said plurality of growth compartments to said first and second ports.

15. The apparatus of claim 13, further comprising a plurality of spacer members positioned to contact the front and back walls of each of said plurality of chambers so that even fluid distribution within said growth chambers is maintained.

16. The apparatus of claim 13, wherein said outlet manifold includes an air filter for aseptic removal of air from the apparatus during treatment.

17. The apparatus of claim 13, wherein closed fluid connections are provided between the supply of fluid and the fluid transportation means, between the fluid transportation means and the inlet manifold, between each outlet port of said inlet manifold and one of said first ports of said chambers, and between each second port of said chambers and one of said inlet ports of said outlet manifold.

18. The apparatus of claim 13, wherein said outlet manifold further comprises an outlet port, said outlet port in fluid communication with an overflow container for accepting excess fluid entering said outlet manifold.

19. The apparatus of claim 13, wherein said outlet manifold further comprises an outlet port, said outlet port in fluid communication with said supply of fluid so as to create a closed fluid loop within the apparatus.

20. The apparatus of claim 15, further comprising a support member for connecting said plurality of spacer members to said inlet and outlet manifolds.

21. The apparatus of claim 20, wherein said support member comprises the spacer members and the inlet and outlet manifolds.

22. An apparatus for promoting growth of cells and tissue, comprising a flexible front and back sheet bonded together along predetermined boundaries wherein:
   a plurality of growth chambers are defined by said flexible front and back sheets bonded together along predetermined boundaries, said growth chambers each configured and dimensioned to house cells or tissue substrates;

at least one internal passageway is defined by said flexible front and back sheets bonded together along predetermined boundaries, said passageway fluidly connecting said plurality of growth chambers; and an inlet port and an outlet port are defined by said flexible front and back sheets bonded together along predetermined boundaries, said inlet and outlet ports fluidly connected to each of said growth chambers by said at least one internal passageway.

23. The apparatus of claim 22, further comprising a frame configured and dimensioned to fit within said bonded front and back sheets, said frame configured in a predetermined pattern so as to further define said growth chambers.

24. The apparatus of claim 22, further comprising a substrate disposed within each of said plurality of growth chambers, wherein each of said substrates is designed to facilitate three-dimensional tissue growth on said substrate.

* * * * *